(12) United States Patent
Hinchliffe

(10) Patent No.: US 6,595,047 B2
(45) Date of Patent: *Jul. 22, 2003

(54) MEASURING INSTRUMENT

(75) Inventor: Malcolm Geoffrey Hinchliffe, Macclesfield (GB)

(73) Assignee: Merlin Partnership, Douglas Isle of Man (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 40 days.

(21) Appl. No.: 09/369,531

(22) Filed: Aug. 6, 1999

(65) Prior Publication Data

US 2001/0011477 A1 Aug. 9, 2001

(30) Foreign Application Priority Data

Aug. 18, 1998 (GB) .............................................. 9817980

(51) Int. Cl.⁷ ................................................ G01L 5/04
(52) U.S. Cl. ...................... 73/159; 73/160; 73/862.391; 73/862.42; 73/862.451
(58) Field of Search ................... 73/160, 159, 862.391, 73/862.42, 862.451, 862.471, 862.73

(56) References Cited

U.S. PATENT DOCUMENTS

| | | | | |
|---|---|---|---|---|
| 4,215,728 A | * | 8/1980 | Weidman et al. | 139/370.2 |
| 4,720,806 A | * | 1/1988 | Schippers et al. | 340/511 |
| 5,001,925 A | | 3/1991 | Turek | 73/160 |
| 5,140,852 A | * | 8/1992 | Bonigk et al. | 73/160 |
| 5,462,094 A | * | 10/1995 | Josefsson et al. | 139/194 |
| 5,664,307 A | * | 9/1997 | Stitz et al. | 28/241 |
| 5,718,854 A | * | 2/1998 | Nguyen | 264/40.1 |
| 5,768,938 A | | 6/1998 | Schilling et al. | 73/160 |
| 5,956,994 A | * | 9/1999 | Schoni | 73/159 |
| 5,966,919 A | * | 10/1999 | Tsou | 57/264 |
| 5,996,925 A | * | 12/1999 | Iwade et al. | 242/413.1 |

FOREIGN PATENT DOCUMENTS

| | | | |
|---|---|---|---|
| GB | 2029023 A | 3/1980 | G01L/5/10 |
| GB | 2127544 A | 4/1984 | G01L/1/10 |
| WO | 96/04100 | 2/1996 | B23Q/16/00 |
| WO | 97/45578 | 12/1997 | D03J/1/04 |

\* cited by examiner

*Primary Examiner*—Hezron Williams
*Assistant Examiner*—Michael Cygan
(74) *Attorney, Agent, or Firm*—Schwegman, Lundberg, Woessner & Kluth P.A.

(57) ABSTRACT

An instrument is provided with several sensing elements to enable several parameters of a processed yarn to be measured or determined. In order to minimize the total sensing element/guide contact with the yarn within the complete process threadline, the yarn is guided through the instrument by contact only with the inlet and outlet guiding elements of the instrument and contact operative sensing elements. One particular instrument consists, in succession, of an interlace sensing device, a tension sensing device and an oil content sensing device. The electrical resistance of the yarn is measured between two pins of the oil content sensing device and in this case, the first pin is also a tension sensing pin of the instrument, and the second pin of the oil content sensing device is also the outlet guide of the instrument.

20 Claims, 1 Drawing Sheet

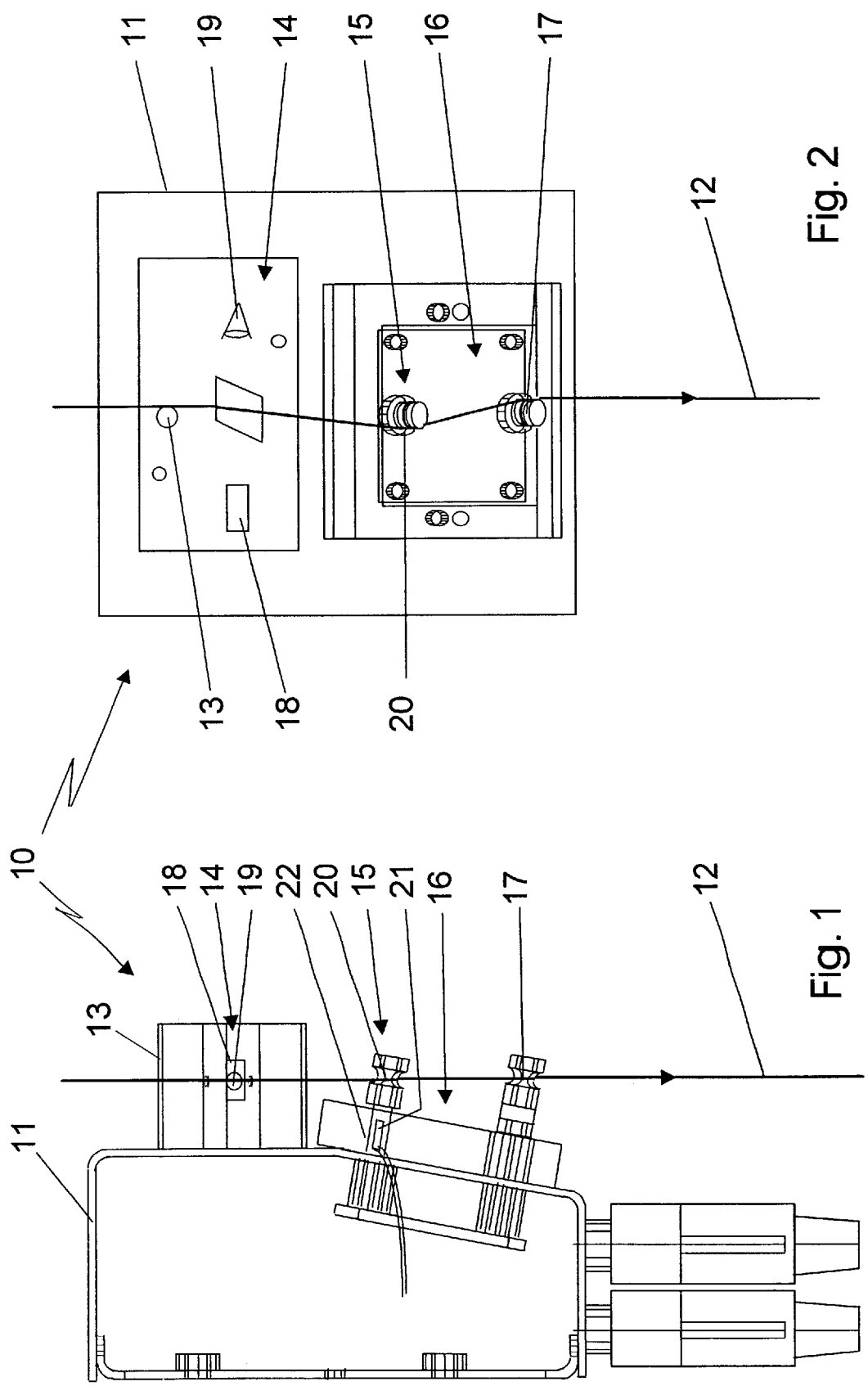

MEASURING INSTRUMENT

FIELD OF THE INVENTION

This invention relates to a measuring instruments for measuring the various parameters of a textile yarn, and in particular to instruments for measuring yarn parameters whilst the yarn is running through a textile machine during the processing of the yarn.

BACKGROUND OF THE INVENTION

There is a requirement to measure various parameters of a textile yarn during and subsequent to the processing of the yarn, to determine the efficiency and effectiveness of such processing and the quality of the processed yarn. To this end, there are many sensing instruments available, each adapted to measure a specific parameter. A typical yarn process on POY or DTY may require the measurement of interlace, oil level and tension and the determination of the presence of broken filaments. To perform all of these measuring or sensing functions requires the use of at least three sensing instruments. Whilst some of the actual operative sensing elements may be non-contact, e.g. optical sensors, each sensing instrument requires two or more yarn contacting sensing elements and/or yarn guides to locate the running yarn in the sensor relative to the operative sensing elements. The result of adding three sensing instruments to a typical process threadline can add over 45° of sensing element/guide wrap, thereby undesirably increasing by a considerable amount the tension in the yarn downstream of those instruments. Hence the quality of the processed yarn is often compromised by the act of monitoring its quality. For this reason, and having regard to the high process speed with some processes, it is desirable or even essential to minimise the total sensing element/guide contact with the yarn within the complete process threadline.

OBJECT OF THE INVENTION

It is an object of the present invention to provide a yarn parameter measuring instrument which minimises the abovementioned problem.

SUMMARY OF THE INVENTION

The invention provides a yarn parameter measuring instrument comprising an inlet yarn guiding element and an outlet yarn guiding element, and a plurality of sensing devices mounted successively within the instrument, each sensing device having at least one operative sensing element adapted to be responsive to a respective yarn parameter, wherein the yarn is guided through the instrument by contact only with the inlet and outlet guiding elements and contact operative sensing elements.

The instrument may comprise a yarn tension sensing device, having an operative sensing element which may comprise a tension sensing pin. The tension sensing pin may have stress measuring means secured thereto adapted to be responsive to the deflection of the tension sensing pin due to the tension in a yarn passing therearound. The stress measuring means may comprise at least one strain gauge secured to a stem which supports the tension sensing pin.

The instrument may comprise an interlace sensing device having operative sensing elements which may comprise a laser beam generating device and a photo diode operable to receive the laser beam.

The instrument may comprise an oil content sensing device, having a first operative sensing element which may comprise a first pin to which an electrical voltage is applied and a second operative sensing element which may comprise a second pin adapted to measure the voltage on the yarn to determine the electrical resistance of the yarn between the first pin and the second pin.

The instrument may comprise, in succession, an interlace sensing device, a tension sensing device and an oil content sensing device. In this case the first pin may be the tension sensing pin, and the second pin may be the outlet guiding element.

BRIEF DESCRIPTION OF THE DRAWINGS

One embodiment of the invention will now be further described with reference to the accompanying drawing in which:

FIG. 1 is a side view of a parameter measuring instrument, and

FIG. 2 is a front view of the instrument of FIG. 1.

DESCRIPTION OF THE PREFERRED EMBODIMENT

Referring now to the Figures, there is shown a yarn parameter measuring instrument 10, having a housing 11 in which there is mounted in succession in the direction of passage of a yarn 12, an inlet guiding element 13, three sensing devices 14, 15 and 16, and an outlet guiding element 17 as described below.

Sensing device 14 is an interlace sensing device which comprises non-contact sensing elements in the form of laser beam generating device 18 and a laser beam receiving photo-diode 19, between which the yarn 12 passes from the inlet guiding element 13. The photo-diode 19 senses changes in the width of the yarn 12 passing through the laser beam, and the resulting signal from the photo-diode 19 is representative of the presence or absence of interlace nodes in the yarn 12.

Sensing device 15 is a tension sensing device which comprises a contact operative sensing element in the form of a tension sensing pin 20 having at least one strain gauge 21 secured to a stem 22 which supports the pin 20 in the housing 11. The signal provided by the strain gauge 21 is a measure of the deflection of the pin 20 under the tension of the yarn 12 passing in contact with it, and hence a measure of that tension.

Sensing device 16 is an oil content sensing device which comprises two contact operative sensing elements in the form of a first pin 20 to which an electrical voltage, e.g. 200 V, is applied and a second pin 17 adapted to measure the voltage on the yarn 12 as it reaches the pin 17 to determine the electrical resistance of the yarn 12 between the pins 20 and 17. This resistance depends upon the oil content of the yarn 12, being high when no oil is present on the yarn 12 and reducing with increasing oil content. In this case the first pin 20 is the tension sensing element of the tension sensing device 15, and the second pin 17 serves also as the outlet guiding element 17.

By means of the invention an instrument is provided which enables several parameters of a processed yarn 12 to be measured or determined. In the above described embodiment, interlace, tension and oil content are measured, but other parameters may be measured or determined in addition to or instead of the those parameters. In order to measure the three parameters as described above using separate instruments, two yarn guides/contact operative elements would normally be provided for each of the interlace and oil content measuring instruments, and three yarn guides/contact operative elements would normally be provided for the tension measuring instrument. These seven yarn guides/contacting elements could require at least 35° and probably over 45° of yarn wrap. In the present case however there are only three yarn guiding/contact operative elements requiring some 15° to 20° of yarn wrap, a reduction of 57%. This will lead to a considerable reduction in output tension in use of the instrument of the present invention by comparison with the use of three separate instruments, and hence considerably less detrimental effect on the quality processed yarn 12 as a consequence of monitoring that quality than has been the case in the past.

What is claimed is:

1. A yarn parameter measuring instrument comprising an inlet yarn guiding element and an outlet yarn guiding element, and a plurality of sensing devices mounted successively within the instrument between the inlet yarn guiding element and the outlet yarn guiding element, each sensing device having at least one operative sensing element adapted to be responsive to a respective yarn parameter, wherein the yarn is guided through the instrument by contact only with the inlet and outlet guiding elements and the sensing elements that are contact operative, the contact operative sensing element of one sensing device serving to guide the yarn to a successive sensing device.

2. An instrument according to claim 1, comprising a yarn tension sensing device.

3. A yarn parameter measuring instrument, comprising an inlet yarn guiding element, an outlet yarn guiding element, a yarn tension sensing device, and a plurality of sensing devices mounted successively within the instrument between the inlet yarn guiding element and the outlet yarn guiding element, wherein each sensing device includes at least one operative sensing element adapted to be responsive to a respective yarn parameter, wherein the yarn is guided through the instrument by contact only with the inlet and outlet guiding elements and the sensing elements that are contact operative, the contact operative sensing element of one sensing element device serving to guide the yarn to a successive sensing device, wherein the yarn tension sensing device has a contact operative sensing element which comprises a tension sensing pin.

4. An instrument according to claim 3, wherein the tension sensing pin has stress measuring means secured thereto responsive to the deflection of the tension sensing pin due to the tension in a yarn passing therearound.

5. An instrument according to claim 4, wherein the tension sensing pin comprises a supporting stem and the stress measuring means comprises at least one strain gauge secured to the stem.

6. A yarn parameter measuring instrument, comprising an interlace sensing device, an inlet yarn guiding element and an outlet yarn guiding element, and a plurality of sensing devices mounted successively within the instrument between the inlet yarn guiding element and the outlet yarn guiding element, each sensing device having at least one operative sensing element adapted to be responsive to a respective yarn parameter, wherein the yarn is guided through the instrument by contact only with the inlet and outlet guiding elements and the sensing elements that are contact operative, the contact operative sensing element of one sensing element device serving to guide the yarn to a successive sensing device.

7. An instrument according to claim 6, wherein the interlace sensing device has operative sensing elements comprising a laser beam generating device and a photo diode operable to receive the laser beam.

8. A yarn parameter measuring instrument, comprising an oil content sensing device, an inlet yarn guiding element and an outlet yarn guiding element, and a plurality of sensing devices mounted successively within the instrument between the inlet yarn guiding element and the outlet yarn guiding element, each sensing device having at least one operative sensing element adapted to be responsive to a respective yarn parameter, wherein the yarn is guided through the instrument by contact only with the inlet and outlet guiding elements and the sensing elements that are contact operative, the contact operative sensing element of one sensing element device serving to guide the yarn to a successive sensing device.

9. An instrument according to claim 8, wherein the oil content sensing device has contact operative sensing elements which comprise a first pin to which an electrical voltage is applied and a second pin adapted to measure the voltage on the yarn to determine the electrical resistance of the yarn between the first pin and the second pin.

10. An instrument according to claim 9, wherein substantially 200 volts are applied to the first pin.

11. A yarn parameter measuring instrument, comprising, in succession, an interlace sensing device, a tension sensing device and an oil content sensing device, and further comprising an inlet yarn guiding element and an outlet yarn guiding element, and a plurality of sensing devices mounted successively within the instrument between the inlet yarn guiding element and the outlet yarn guiding element, each sensing device having at least one operative sensing element adapted to be responsive to a respective yarn parameter, wherein the yarn is guided through the instrument by contact only with the inlet and outlet guiding elements and the sensing elements that are contact operative, the contact operative sensing element of one sensing element device serving to guide the yarn to a successive sensing device.

12. An instrument according to claim 11, wherein the oil content sensing device has contact operative sensing elements which comprise a first pin to which an electrical voltage is applied and a second pin adapted to measure the voltage on the yarn to determine the electrical resistance of the yarn between the first pin and the second pin, and wherein the first pin is a tension sensing pin, and the second pin is the outlet guiding element.

13. The instrument of claim 1, wherein the plurality of sensing devices includes a contact sensing device and a non-contact sensing device.

14. The instrument of claim 1, wherein the inlet yarn guiding element, an outlet yarn guiding element and the plurality of sensing devices cause only about 15 degrees to about 20 degrees of yarn wrap.

15. The instrument of claim 3, wherein the inlet yarn guiding element, an outlet yarn guiding element and the plurality of sensing devices cause only about 15 degrees to about 20 degrees of yarn wrap.

16. The instrument of claim 6, wherein the inlet yarn guiding element, an outlet yarn guiding element and the plurality of sensing devices cause only about 15 degrees to about 20 degrees of yarn wrap.

17. The instrument of claim 8, wherein the inlet yarn guiding element, an outlet yarn guiding element and the plurality of sensing devices cause only about 15 degrees to about 20 degrees of yarn wrap.

18. The instrument of claim 11, wherein the inlet yarn guiding element, an outlet yarn guiding element and the plurality of sensing devices cause only about 15 degrees to about 20 degrees of yarn wrap.

19. A yarn parameter measuring instrument, comprising:
an inlet yarn guiding element;
an outlet yarn guiding element; and
a plurality of sensing devices mounted successively within the instrument between the inlet yarn guiding element and the outlet yarn guiding element, each of the plurality of sensing devices being operative to measure a respective yarn parameter different from the other of the plurality of sensing devices, each sensing device having at least one operative sensing element adapted to be responsive to the respective yarn parameter, wherein the yarn is guided through the instrument by contact only with the inlet and outlet guiding elements and the sensing elements that are contact operative, the contact operative sensing element of one sensing device serving to guide the yarn to a successive sensing device.

20. The instrument of claim 19, wherein the inlet yarn guiding element, an outlet yarn guiding element and the plurality of sensing devices cause only about 15 degrees to about 20 degrees of yarn wrap.

* * * * *